United States Patent [19]
Wong et al.

[11] Patent Number: 5,585,252
[45] Date of Patent: Dec. 17, 1996

[54] ENANTIO- AND REGIOSELECTIVE SYNTHESIS OF ORGANIC COMPOUNDS USING ENOL ESTERS AS IRREVERSIBLE TRANSACYLATION REAGENTS

[75] Inventors: Chi-Huey Wong; Yi-Fong Wang, both of College Station; Wiliam J. Hennen, Bryan, all of Tex.

[73] Assignee: G. D. Searle & Co., Chicago, Ill.

[21] Appl. No.: 309,716

[22] Filed: Sep. 21, 1994

Related U.S. Application Data

[63] Continuation of Ser. No. 945,196, Sep. 15, 1992, abandoned, which is a continuation of Ser. No. 704,687, May 17, 1991, abandoned, which is a continuation of Ser. No. 238,358, Aug. 30, 1988, abandoned.

[51] Int. Cl.$^6$ ............... C12P 19/44; C12P 19/28; C12P 7/62; C12P 7/40
[52] U.S. Cl. ............... 435/85; 435/280; 435/74; 435/135; 435/136; 435/147
[58] Field of Search ............... 435/280, 74, 85, 435/135, 136, 147

[56] References Cited

U.S. PATENT DOCUMENTS 5,106,750  4/1992  Wong et al. ............... 435/280

FOREIGN PATENT DOCUMENTS 0357009  8/1989  European Pat. Off. .

OTHER PUBLICATIONS

Riva et al. (1988). *J. Am Chem Soc.*, (110) 549–589.
Sweers et al. (1986) *J. of the American Chemical Society.* (108). pp. 6421–6422.
Wang et al. (1988) *Journal of Organic Chemistry* (53), pp. 3127–3129.
Degueil–Castaing et al (1987) *Tetrahedron Letters* (28), pp. 953–954.
Wang et al. (1988) *J. Am Chem Soc* (110), pp. 7200–7205.

*Primary Examiner*—John W. Rollins
*Assistant Examiner*—Francisco C. Prats
*Attorney, Agent, or Firm*—Cynthia S. Kovacevic; Roger A. Williams

[57] ABSTRACT

A process for irreversible regio- and stereoselective enzyme catalyzed acylation of alcohols using enol esters as acylating reagents is disclosed. The present invention permits the selective modification of hydroxyl group(s) of chiral and meso alcohols, including sugars, organometallics, and glycosides. The enol freed upon transesterification rapidly tautomerizes to the corresponding volatile aldehyde or ketone thereby preventing the reverse reaction from occurring.

20 Claims, No Drawings

ENANTIO- AND REGIOSELECTIVE SYNTHESIS OF ORGANIC COMPOUNDS USING ENOL ESTERS AS IRREVERSIBLE TRANSACYLATION REAGENTS

This is a file-wrapper continuation of application Ser. No. 07/945,196, filed Sep. 15, 1992, now abandoned, which is a continuation of application Ser. No. 07/704,687, filed May 17, 1991, now abandoned, which is a continuation of application Ser. No. 07/238,358, filed Aug. 30, 1988, now abandoned.

BACKGROUND OF THE INVENTION

The present invention relates to enantio- and regioselective synthesis of esters of alcohols, sugars, organometallics and glycosides and to their preparation using enzyme mediated transesterification. More particularly, the present invention relates to enzyme catalyzed irreversible transesterification using enol esters as transacylation reagents.

Hydrolytic enzymes such as lipases, esterases, and proteases have been used extensively as catalysts in enantioselective syntheses. Whitesides, G. M., Wong, C-H. *Angew. Chem. Int. Ed. Engl.* 24 (1985) 617; Jones, J. B. *Tetrahedron* 42 (1986) 3351; Roberts, S. M. *Chem. Br.* (1987) 127; Akiyama, A., Bednarski, M., Kim, M. J., Simon, E. S., Waldmann, H. I., Whitesides, G. M. *Ibid.* (1987) 645. Because of their relatively high stability in organic media, many hydrolytic enzymes also can be used in organic solvents for certain types of transformations which are difficult to do in water. The most common reactions are esterase and lipase-catalyzed stereoselective esterifications and transesterifications. Klibanov, A. M. *CHEMTECH* (1986) 354–9; Klibanov, A. M., Cambou, B. *J. Am. Chem. Soc.* 106 (1984) 2687–92. Chen, C-S., Wu, S-H., Girdaukas, G., Sih, C. J. *J. Am. Chem. Soc.* 109 (1987) 2812–17; Guo, Z. W., Sih, C. J. *Ibid.* 110 (1988) 1999–2001; Gil, G., Ferre, E., Meou, A., Petit, J. L., Triantaphylides, C. *Tetrahedron Lett.* 28 (1987) 1647; Yokozeki, K., Yamanaka, S., Takinami, K., Hirose, Y., Tanaka, A., Sonomoto, K., Fukui, S. *Eur. J. Appl. Microbiol. Biotechnicol* 14 (1982) 1; Tambo, G. M. R., Schar, H-P., Busquets, X. F., Ghisalba, O. *Tetrahedron Lett.* 27 (1986) 5705–10; Belan, A., Bolte, J., Fauve, A., Gourey, J. G., Veschambre, H. *J. Org. Chem.* 52, 256–60. Langrand, G., Baratti, J., Buono, G., Triantaphylides, C. *Tetrahedron Lett.* 27 (1986) 29–32.

One disadvantage of enzyme catalyzed hydrolytic reactions is that they are very slow compared to simple hydrolyses. Langrand, G., Baratti, J., Buono, G., Triantaphylides, C. *Tetrahedron Lett.* 27 (1986) 29–32. In addition, the products produced by enzymatic hydrolyses very often have to be separated from other by-products (particularly alcohol generated from the acylating reagent). Due to the reversible nature of these reactions, and due to the same stereoselectivity of the enzyme catalysis in both directions, the optical purity of the product obtained decreases as the reverse reaction proceeds. This situation is illustrated in FORMULA 1 where a racemic alcohol is to be resolved via an enzymatic esterification (R"=H) or transesterification.

FORMULA 1

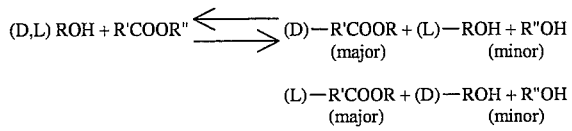

As shown in FORMULA 1, if the D-isomer is a better substrate than the L-isomer for the enzyme, accumulation of the D-ester and the unreactive L-alcohol will be observed. In the reverse reaction, however, the D-ester is a better substrate and will be converted to the D-alcohol. The enantiomeric excess of both the D-ester and the L-alcohol therefore will decrease progressively as the extent of the reverse reaction increases. This reverse reaction problem clearly has been illustrated in the kinetic resolution of menthol, Chen, C-S., Wu, S-H., Girdaukas, G., Sih, C. J. *J. Am. Chem. Soc.* 109 (1987) 2812–17; Guo, Z. W., Sih, C. J. *Ibid.* 110 (1988) 1999–2001, and can be seen in the enantioselective esterification or transesterification of meso compounds.

SUMMARY OF THE INVENTION

The method of the present invention blocks the progress of the reverse reaction. The present invention is a process for irreversible regio- and stereoselective enzyme catalyzed acylation of alcohols using enol esters as acylating reagents. The present invention permits the selective modification of hydroxyl group(s) of chiral and meso alcohols, including sugars, organometallics and glycosides. The enol freed upon transesterification rapidly tautomerizes to the corresponding volatile aldehyde or ketone thereby preventing the reverse reaction from occurring.

DETAILED DESCRIPTION OF THE INVENTION

Nuclear magnetic resonance (NMR) spectra were recorded on a Varian XL-200E spectrometer. All chemical shifts were reported in ppm using tetramethylsilane as an internal standard unless otherwise indicated. Rotations were determined on a Perkin Elmer 240 polarimeter. Gas chromatographic (GC) analyses were performed on a Hewlett-Packard 5890 instrument with a 20-m DB-5 megabore column. The lipases from PSEUDOMONAS species (PSL, Type XIII), porcine pancreas (PPL, Type II), and CANDIDA CYLINDRACEA (CCL, Type VII) were obtained from Sigma Chemical Company. Cholesterol esterase was obtained from Amano Pharmaceutical Company. Vinyl acetate ($5/Kg, bp 72° C.) and isopropenyl acetate ($25/Kg, bp 94° C.) were from Aldrich Chemical Co. Vinyl propionate ($25/25 g, bp 93°–94° C.) was from Pfaltz and Bauer, Inc. Some experimental protocols are described in Tables 1, 3 and 4.

The procedure for preparation of isopropenyl valerate (1b of FORMULA 2) was similar to that reported for the preparation of other isopropenyl esters, with some modifications. Rothman, E. S., Serota, S., Peristein, T., Swern, D. *J. Org. Chem.* 27 (1962) 3123–27. To a 250 mL round bottom flask was added 10 mL of valetic acid (91.9 mmol) which had been freshly distilled, and 20 mL of valetic anhydride. Then, 200 mL of freshly distilled isopropenyl acetate was added followed by 2 drops of concentrated sulfuric acid. The mixture then was heated to reflux under an atmosphere of argon for 10 h, after which time all of the valetic acid had been consumed as evidenced by capillary GC. The reaction mixture was allowed to cool to room temperature and 0.5 g of sodium bicarbonate was added to quench the acid catalyst. The isopropenyl acetate then was removed by evaporation under reduced pressure. The orange liquid remaining was poured into 300 mL of 0° C. saturated sodium bicarbonate which was overlayed with 100 mL of diethyl ether. The mixture was stirred vigorously and the ether layer was analyzed by GC for the disappearance of the mixed valetic acetic anhydride. After all of the anhydride was consumed (6 h) the ether layer was separated and the aqueous layer was washed with 100 mL of ether. The combined ether layers were washed with 5×25 mL portions of saturated sodium bicarbonate to remove the valetic acid. The ether layer then was washed with saturated brine (30 mL) and the ether was then dried over sodium sulfate. The ether was removed under reduced pressure and the isopropenyl ester was purified by vacuum distillation (bp=50°–52° C., 8 mm Hg). 7.85 g of a clear colorless liquid (1b) was obtained (60.1% yield). $^1$H-NMR (CDCl$_3$) 4.65 (m, 2H), 2.35 (t, 2H) 1.90 (s, 3H), 1.65 (m, 2H), 1.35 (m, 2H), 0.90 (s, 3H). $^{13}$C-NMR 171.89, 153.00, 101.87, 34.02, 26.92, 22.16, 19.52, 13.16. In a similar manner isopropenyl butyrate was prepared from burytic acid in 54% yield. 3.68 g of isopropenyl butyrate were prepared from 4.85 mL of butyric acid and 10 mL of burytic anhydride. $^1$H-NMR 4.60 (m, 2H), 2.30 (t, 2H), L.85 (s, 3H), 1.60 (m, 2H), 0.90 (t, 3H).

The method of Swern and Jordan was used to prepare vinyl valerate (1e of FORMULA 2). Swern, D., Jordan, E. F. *Organic Synthesis*, Coll. Vol. IV (1963) 977–80, incorporated herein by reference. Freshly distilled valeric acid (40 mL, 0.37 mol) and vinyl acetate (300 mL) were placed in a 3-necked 500 mL round bottomed flask fitted with a reflux condenser, a gas inlet tube and a thermometer. The solution was stirred under argon and mercuric acetate (1.2 g, 0.37 mmol) was added. The reaction mixture was stirred under argon for 30 min, after which time 10 drops of 100% sulfuric acid was added. The solution was heated to reflux for 6 h and then was allowed to cool to room temperature. Sodium acetate (1.0 g) was added to quench the acid catalyst. The excess vinyl acetate was removed by distillation under argon. The product (vinyl valerate) 1e was isolated by distillation (bp=135°–145° C.) as a clear colorless liquid (29.4 g, 62% yield). $^1$H-NMR 7.24 (m, 1H), 4.80 (m, 1H), 4.48 (m, 1H), 2.32 (t, 2H), 1.60 (m, 2H), 1.30 (m, 2H), 0.85 (t, 3H). $^{13}$C-NMR 170.69, 141.11, 97.22, 33.54, 26.57, 22.10, 13.57.

Any chiral or meso alcohol having no excessive steric hindrance can be used in the present method. Structures 15 and 16 of Table 2 represent compounds wherein excessive steric hindrance is present.

Lipase-Catalyzed Reactions

A number of lipase-catalyzed irreversible transesterifications using enol esters as acylating reagents were performed in a manner outlined generally in FORMULA 2.

$$R_1 \overset{O}{\underset{}{\parallel}} O \overset{O}{\underset{}{\parallel}} R_2 + ROH \longrightarrow R_1 \overset{O}{\underset{}{\parallel}} OR + R_2 \overset{O}{\underset{}{\parallel}} CH_3$$

| | $R_1$ | $R_2$ | |
|---|---|---|---|
| 1a | CH$_3$— | CH$_3$ | isopropenyl acetate |
| 1b | CH$_3$(CH$_2$)$_3$— | CH$_3$ | isopropenyl valerate |
| 1c | CH$_3$— | H | vinyl acetate |
| 1d | CH$_3$CH$_2$— | H | vinyl propionate |
| 1e | CH$_3$(CH$_2$)$_3$— | H | vinyl valerate |

FORMULA 2

The reactions produced optically active esters from several alcohols including those from glycerol and serinol derivatives, organometallics, nucleoside derivatives, sugars, and other chiral and racemic alcohols. The results are capsulized in Table 1.

TABLE 1

Lipase-catalyzed transesterifications with enol esters as acylating agents.

| Entry | Substrate | Enz | enol ester | % conversion | % ee alcohol (Config.) | % ee ester (Config.) |
|---|---|---|---|---|---|---|
| 1 | 2 | PSL | 1a | 72 | — | 96 (S) |
| 2 | 5 | PPL | 1e | 60 | — | 97 (R) |
| 3 | 8a | PSL | 1a | 32 | 29 (S) | 67 (R) |
| 4 | 8b$^a$ | PSL | H$_2$O | 50 | 92 (R) | — |
| 5 | 8a | PSL | 1b | 25 | 21 (S) | 64 (R) |
| 6 | 8a | ChE | 1a | 33 | 22 (S) | 54 (R) |
| 7 | 8a | CCL | 1a | 21 | 14 (S) | 50 (R) |
| 8 | 9a | PPL | 1d | 43 | — | 54 (S) |
| 9 | 9a | PPL | 1e | 45 | — | 39 (S) |
| 10 | 9a | PSL | 1d | 50 | — | 18 (S) |
| 11 | 10a | PPL | 1d | 40 | — | 33 (S) |
| 12 | 10a | PPL | 1c | 40 | — | 42 (S) |
| 13 | 10b$^a$ | PPL | H$_2$O | 30 | 82 (S) | — |
| 14 | 10a | PPL | 1c | 80 | 65 (R) | — |
| 15 | 10a | PPL | 1e | 40 | — | 30 (S) |
| 16 | 10a | ChE | 1a | 31 | 4 (R) | 10 (S) |
| 17 | 11a | PSL | 1c | 30 | — | 70 (R) |
| 18 | 11b$^a$ | PSL | H$_2$O | 60 | 94 (R) | — |
| 19 | 12a | CCL | 1e | 30 | — | 37 (R) |
| 20 | 13a | PPL | 1c | 37 | 56 (S) | 98 (R) |
| 21 | 13a | PPL | 1c | 58 | >98 (S) | 71 (R) |
| 22 | 14a | PPL | 1c | 27 | 37 (S) | 98 (R) |
| 23 | 14a | PPL | 1c | 62 | '98 (S) | 61 (R) |
| 24 | 15 | CCL | 1c | — | — | — |
| 25 | 16 | CCL | 1c | — | — | — |
| 26 | 17a | PPL | 1d | 40 | — | 84 (R) |
| 27 | 17a | PPL | 1d | 60 | 84 (S) | — |

$^a$The obtained optically active ester was used as substrate in hydrolysis in 0.1 M phosphate buffer (pH 7) at 28° C. The pH was controlled at 7.0 during the reaction by addition of 1 N NaOH. Monitoring of the reaction progress and isolation of the products were the same as that in transesterification reactions.

The reaction schemes for enantioselective acylation of 2-O-benzylglycerol (2) and N-carbobenzoxy serinol (5) are shown in FORMULAE 3 and 4, respectively. The calculated kinetic parameters α and E are also listed.

FORMULA 3

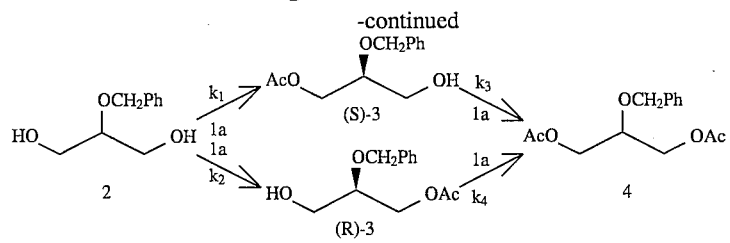
For PSL: $\alpha = 5.6 = k_1/k_2$    $E_1 = 0.033 = k_3/(k_1 + k_2)$
$E_2 = 0.2 = k_4/(k_1 + k_2)$
FORMULA 4
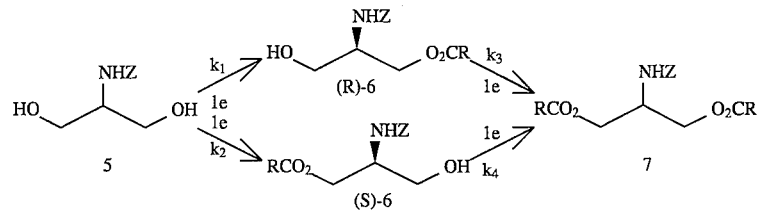
For PPL: $\alpha = 8.8 = k_1/k_2$,    $E_1 = 0.02 = k_3/(k_1 + k_2)$
$E_2 = 0.35 = k_4/(k_1 + k_2)$
Table 2 diagrams the starting materials and products formed from the reactions listed in Table 1, entries 3–27.
The general procedure used in the following lipase catalyzed transesterifications was as follows:
TABLE 2
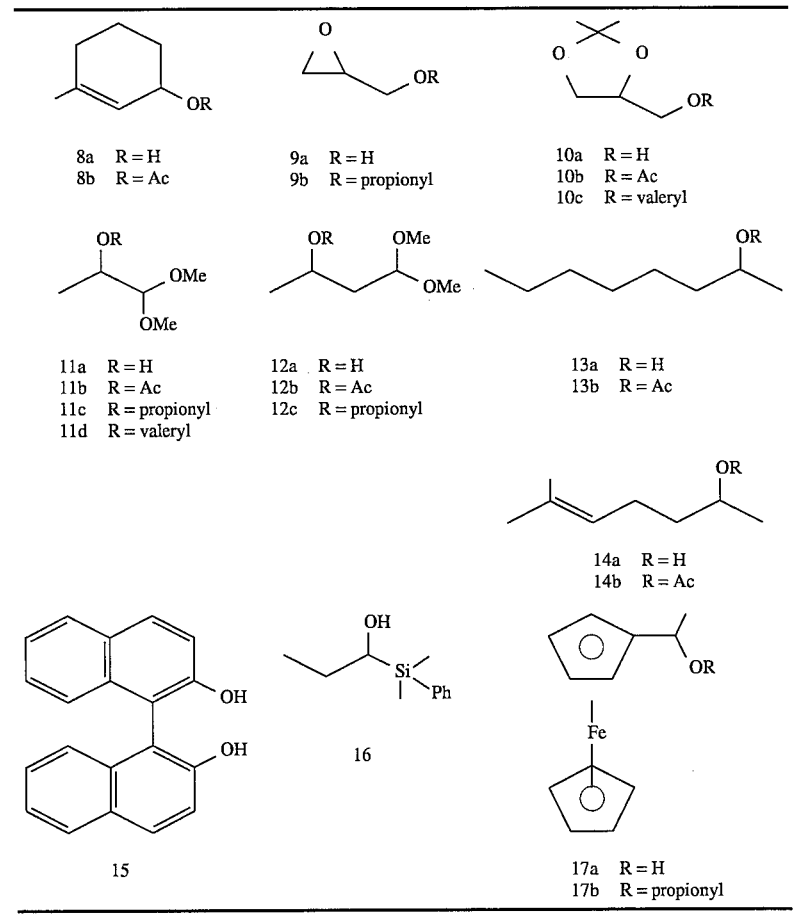

The alcohol substrate and an excess of enol ester were dissolved in an organic solvent, such as pyridine or a less polar solvent. After a catalytic amount of enzyme was added, the suspension was stirred at 28° C. and the reaction was monitored by GC for conversion. Once the required extent of conversion was reached, the enzyme was filtered off and the solvent was removed by evaporation in a vacuum. The ester product and the unreacted alcohol were separated by chromatography on a silica gel column.

Some of the esters (e.g, acyl sugars) that were prepared can be obtained only in nearly anhydrous solvents due to thermodynamic reasons, or because of the lack of appropriate esterases to use in obtaining such esters via hydrolysis (e.g., (S)-3 in FORMULA 3 and (R)-6 in FORMULA 4). For example, in the kinetic resolution of ferrocenylethanol, the (R)-propionate ester obtained in toluene is stable towards solvolysis, while in ethanol or water, the ester decomposes to ferrocenylethylether or ferrocenylethanol.

Transesterification of symmetrically prochiral diols

EXAMPLE 1

PSL-catalyzed transesterification of 2-0-benzylglycerol (2 of FORMULA 3) with isopropenyl acetate (1a of FORMULA 2)

Chiral 3-0-acetyl-2-0-benzylglycerol ((R)- or (S)-3 of FIG. 3), and 3-0-acetyl-2-N-benzyloxycarbonyl serinol ((R) or (S) -6 of FORMULA 5), are considered to be useful building blocks for the preparation of enantiomerically pure, biologically active molecules such as phospholipids, PAF (platelet-activating factor), phospholipase A2 inhibitors, sphingoglycolipids and many others. To prepare these chiral synthons, the prochiral diols, 2-0-benzylglycerol (2 of FORMULA 3) and 2-N-benzyloxycarbonyl (Z) serinol (5 of FORMULA 4) were chosen as substrates, respectively.

(a) A solution of 2-0-benzylglycerol (2 of FORMULA 3) (300 mg, 1.65 mmol) and isopropenyl acetate (1a of FORMULA 2) (0.73 mL, 6.6 mmol) in 4 mL of chloroform was mixed with 10 mg of PSL. After 27 h, the amounts of diacetate, monoacetate and diol were quantitatively determined to be 43:57:0 by GC analysis. The reaction was terminated and worked up as described in the general procedure. The products were separated by column chromatography (ethyl acetate:n-hexane—1:3) on silica gel to give 196 mg (53%) of monoacetate ((S)-3 in FORMULA 3), $[\alpha]_D^{23}$ 20.1 (c 1, CHCl$_3$), and 175 mg of diacetate (4 in FORMULA 3). Monoacetate (S)-3: $^1$H-NMR 2.08 (3H, s), 3.60–3.78 (3H, m), 4.23 (2H, d, J=4.8 Hz), 4.61 (1H, d, J=11.8 Hz), 4.72 (1H, d, J=11.8 Hz), 7.35 (5H, s). Diacetate 4 in FORMULA 3: $^1$H-NMR 2.06 (6H, s), 3.81 (1H, tt, J=5.2 Hz), 4.15 (2H, dd, J=5.2 Hz and 11.8 Hz), 4.25 (2H, dd, J=5.2 Hz and 11.8 Hz), 4.66 (2H, s), 7.34 (5H, s). The optical purity of monoacetate (15 mg) was determined to be 96% by $^1$H-NMR spectroscopy in the presence of Eu(hfc)$_3$ (30 mg). The relative intensities of the acetoxy group at 3.05 (major) and 2.90 (minor) were used for ee determination.

(b) A solution of 2-0-benzylglycerol (2 of FORMULA 3) (3 mmol) and isopropenyl acetate (1a of FORMULA 2) (12 mmol) in 6 mL of chloroform was mixed with 12 mg of the lipase from PSEUDOMONAS (PSL) species at 28° C. with stirring. After 24 h, the amounts of diacetate, monoacetate and diol were quantitatively determined to be 10.0:82.6:7.4. The products were separated by column chromatography on silica gel to afford 538 mg (80%) of monoacetate ((S)-3 of FORMULA 3), the optical purity of which was determined to be 75.5% by $^1$H-NMR spectroscopy in the presence of tris (3-(hepta-fluoropropylhydroxymethylene)-(+)-camphorato] europium (III) derivative (Eu(hfc)$_3$). The monoacetates produced in the transesterification reaction were expected to undergo further acetylation to yield the diacetate (4 of FORMULA 3) and the enzyme was expected to show the same stereo-chemical preference in the second step (i.e. $k_4$>$k_3$) as in the hydrolysis of meso diacetate compounds, so that the optical purity of monoacetate (S)-3 could be enhanced by increasing the conversion. Wang, Y. F., Chen, C. S., Girdaukas, G., Sih, C. J. *J. Am. Chem Soc.* 106 (1984) 3695; Wang, Y. F., Sih, C. J. *Tetrahedron Lett.* 25 (1985) 4999.

To determine the constants, the diols, monoesters, and diesters were determined by GC analysis at a certain degree of conversion. The enantiomeric compositions of monoesters were determined by NMR analysis. As predicted, when the reaction was terminated at 71.5% conversion (a 50% conversion corresponds to the hydrolysis of one acetate group), the optical purity of the monacetate (S)-3 obtained was 96% (the isolated chemical yield was 53%).

The reported rotations of ((R)-3 of FORMULA 3) are not in agreement with our values. The reported rotation of (R)-3 prepared through a lipoprotein lipase-catayzed hydrolysis of diacetate (4 of FORMULA 3) was $[\alpha]_D^{20}$–13.2 (c 3, EtOH), 91% ee. Breitgoff, D., Laumen, K., Schneider, M. P., *JCS Chem. Comm.* (1986) 1523. Another reported value was $[\alpha]_D^{25}$ +15.0 (c 2, CHCl$_3$) or –12.3 (c 1.8, EtOH); Kerscher, V., Kreiser, W., *Tetrahedron Lett.* 28 (1987) 531. Based on the rotation of the enantiomer prepared in the present reaction, the specific rotation of R-3 corresponds to 77% ee.

The kinetics of these irreversible transesterifications can be treated as similar to the kinetics Of hydrolysis, and the equation developed by Sih et al. for use in prediction of ee rs. conversion in hydrolysis should be applicable here. Wang, Y. F., Chen, C. S., Girdaukas, G., Sih, C. J. *J. Am. Chem. Soc.* 106 (1984) 3695; Wang, Y. F., Sih, C. J. *Tetrahedron Lett.* 25 (1985) 4999. To determine the constants, the diols, monoesters, and diesters were determined by GC analysis at certain degree of conversion. The enantiomeric compositions of monoesters were determined by NMR analysis. Indeed, the kinetic constants for the transesterification of 2-O-benzylglycerol (2 of FORMULA 3) using PSL were determined to be $\alpha=k_1/k_2=5.6$, $E_1=k_3/(k_1+k_2)=0.02$, $E2=k_4(k_1+k_2)=0.33$. Wang, Y. F., Chen, C. S., Girdaukas, G., Sih, C. J. *J. Am. Chem Soc.* 106 (1984) 3695; Wang, Y. F., Sih, C. J. *Tetrahedron Lett.* 25 (1985) 4999.

To determine the absolute stereochemistry of the monoacetate, it was converted to 2,2-dimethyl-1,3-dioxolane-4-methanol (glycerol acetonide) according to the procedures of Suemune, H., Mizuhara, Y., Akita, H., Sakai, K. *Chem. Pharm. Bull*, 34 (1986) 3440–44; Hirth, G., Barner, R. *Helv. Chim. Acta* 65 (1982) 1059 (platelet-activating factor). The resulting glycerol acetonide was the "R" configuration based on rotation, indicating that the monacetate obtained had the "S" configuration. It has been reported that (R)-3 can be prepared from 2-0-benzylglycerol diacetate via a lipoprotein lipase-catalyzed hydrolysis. The same enantioselectivity in the hydrolysis of the diacetate (4 of FORMULA 3) was observed with PSL and (R)-3 was obtained in 52% yield with 71% ee. When (S)-3 (91% ee) was suspended in phosphate buffer (0.1M, pH 7) at 28° C. without enzyme, the optical purity was found to decrease 2–2.5% per hour. These two irreversible enzymatic processes thus provide a new route to (R)- and (S)-3.

EXAMPLE 2

PPL-catalyzed transesterification of 2-N-benzyloxycarbonyl (Z) serinol (5 of FORMULA 4) with vinyl valerate )1e of FORMULA 2)

A solution of 2-N-benzyloxycarbonyl (Z) serinol (5 of FORMULA 4) (225 mg, 1 mmol) and vinyl valerate (1e of FORMULA 2) (512 mg, 4 mmol) in 22.5 mL of THF was incubated with 900 mg of PPL at 28° C. with stirring. After 11 hours, the reaction was terminated. The products were separated by silica gel column chromatography (ethyl acetate: n-hexane=1:4→1:1) to afford 238 mg (77%) of monovalerate (R)-6 of FORMULA 4, $[\alpha]^{23}_D$ +3.2 (c 1.0, $CHCl_3$), and 75 mg of divalerate 7 of FORMULA 4. Monovalerate (R)-6 of FORMULA 4: $^1$H-NMR 0.91 (3H, t, J=7.2 Hz), 1.34 (2H, tq, J=7.2, 7.2 Hz), 1.60 (2H, tt, J=7.2, 7.2 Hz), 2.33 (2H, t, J=7.2 hz), 3.65 (2H, m), 3.94 (1H, m), 4.23 (2H, d, J=5.6 Hz), 5.11 (2H, s), 5.2 (1H, br), 7.36 (5H, s). Divalerate (7 of FORMULA 5): $^1$H-NMR 0.91 (6H, t, J 7.2 Hz), 1.33 (4H, tq, J=7.2, 7.2 Hz), 1.59 (4H, tt, J=7.2, 7.2 Hz), 2.31 (4H, t, J=7.2, 7.2 Hz), δ4.02≅4.30 (5H, m), 5.11 (7H, s), 5.05≅5.20 (1H, br), 7.36 (5H, s). To determine the optical purity of monovalerate R-6, R-6 was treated with (+)-2-methoxy-2-(trifluoromethyl)phenylacetyl chloride [(+)-MTPA chloride] and the resulting (+)-MTPA ester (20 mg), which was analyzed by $^1$H-NMR spectroscopy in the presence of $Eu(hfc)_3$ (80 mg) to establish an enantiomeric excess (ee) greater than 97%. The relative intensities of benzylic methylene group at 4.8 (major) and 4.6 (minor) were measured for ee determination.

EXAMPLE 3

PSL-catalyzed transesterification of seudenol (8a in Table 2) with isopropenyl acetate (1a of FORMULA 2)

Compound 8a has been used in natural product synthesis via radical-mediated cyclization. Stork, G., Sofia, M. J. *J. Am. Chem. Soc.* 108 (1986) 6826–28. A solution of isopropenyl acetate (0.44 mL, 4 mmol) and seudenol 8a (224 mg, 2 mmol) in 2 mL of n-hexane was mixed with 3 mg of PSL at 28° C. with stirring. After 20 hours, the amounts of seudenol acetate 8b and seudenol 8a were quantitatively determined to be 32:68 by GC analysis. The reaction mixture was worked up as usual and the products were separated by silica gel column chromatography (dichloromethane: n-hexane=1:3→1:0) to afford 91 mg (29.5%) of acetate 8b, $[\alpha]^{23}_D$ +138.3 (c 0.8, $CHCl_3$) and 138 mg (61.8%) of alcohol 8a, $[\alpha]^{23}_D$ −26.7 (c 1.5, $CHCl_3$). Acetate 8b: $^1$H-NMR 1.6≅2.0 (6H, m), 1.71 (3H, s), 2.03 (3H, s), 5.24 (1H, m), 5.47 (1H, m). The optical purity of monoacetate (+) 8b (9 mg) was determined to be 67% ee by $^1$H-NMR spectroscopy in the presence of $Eu(hfc)_3$ (57 mg). The relative intensities of the methyl group in double bond at 2.27 (major) and 2.31 (minor) were measured for ee determination. The alcohol (−)-8a was converted to the corresponding acetate by treatment of acetic anhydride in pyridine and then analyzed by the same procedure: ee=29%. 8a and 8b were assigned the designations of "S" and "R", respectively, based on their rotations compared to the reported values. Mori, K., Hazra, B. G., Pfeiffer, R. J., Gupta, A. K., Lindgren, B. S. *Tetrahedron Lett.* 43 (1987) 2249–54.

EXAMPLE 4

PPL-catalyzed transesterification of glycidol (9a in Table 2) with vinyl propionate (1d in FORMULA 2)

To a 100 mL round bottomed flask was added glycidol (9a in Table 2) (2.3 g, 31 mmol), vinyl propionate (1d in FIG. 2) (7.0 g, 70 mmol), toluene (0.61 g) as an internal standard, and 80 mL of chloroform. The enzyme (PPL, 5 g) was suspended in the reaction mixture and the suspension was stirred. At 43% conversion (3.5 h), 5 g of celite was added to the suspension and the mixture was filtered. The filtrate was extracted with three 15 mL portions of distilled water and then washed once with 15 mL of saturated brine. The solvent was removed under reduced pressure and a yellow oil was obtained corresponding to pure glycidol propionate (9b in Table 4) (0.95 g, 23.2% yield from racemic glycidol). The optical purity as determined by $Eu(hfc)_3$ was 54%, while the optical rotation was found to be +15.2 (c 4, chloroform) corresponding to an optical purity of 53.5% (lit. for R ester is −28.4° C.)[25]. $^1$H-NMR 4.05 (dd, 1H), 3.90 (dd, 1H), 3.24 (m, 1H), 2.85 (m, 1H), 2.65 (m, 1H), 2.35 (q, 3H), 1.15 (t, 3H), $^{13}$C-NMR 174.19, 64.83, 49.38, 44.65, 27.33, 9.01.

EXAMPLE 5

PPL-catalyzed transesterification of solketal (10a in Table 2) with vinyl esters In a representative procedure, 1 g of solketal (10a in Table 2) (7.5 mmol) and 2.3 g of vinyl acetate (1c in FIG. 2) (26.7 mmol) in 50 mL of chloroform was incubated with PPL (2 g) along with 0.5 g of hexane as an internal standard. After the reaction had proceeded to 40% conversion, the mixture was worked up as usual to give the ester with an optical purity of 42% by analysis with $Eu(hfc)_3$. The relative intensities of the methyl group of the isopropyl group at 2.63 (major) and 2.57 (minor) were measured to determine ee. In a similar manner the esterificiation was allowed to proceed to 80% conversion and the unreacted alcohol was isolated as described above. solketal acetate 10b was found to have an optical purity of 65% ee. Solketal acetate 10b: $^1$H-NMR 4.40 (m, 1H), 4.05 (m, 3H), 2.72 (m, 1H), 2.07 (s, 3H), 1.35 (s, 3H).

EXAMPLE 6

PSL-catalyzed transesterification of 2-hydroxypropanal dimethyl acetal (11a in Table 2) and 3-hydroxybutanal dimethyl acetal (12a in Table 2)

Optically active 11a and 12a of Table 2 are useful as substrates in aldolase-catalyzed synthesis of novel sugars. Durrwachter, J. R., Wong., C-H. *J. Org. Chem.*, submitted. To a stirred solution of 2-hydroxypropanal dimethyl acetal (11a of Table 2) (480 mg, 4 mmol) and vinyl acetate (1c of FIG. 2) (20 mmol) in petroleum ether (20 mL) was added 9.6 mg of PSL. After the reaction had proceeded to 30%, the reaction suspension was treated as described in the general procedure. The products were separated on a silica gel column (petroleum ether: ethyl acetate=9:1→3:1). 2-acetoxy-propanal dimethyl acetal 11b: $^1$H-NMR ($CDCl_3$); 1.16 (3H d, J=5.5 Hz); 2.00 (3H, s); 3.33 (3H, s); 3.36 (3H, s); 4.20 (1H, d, J=5.5 Hz); 4.80≅4.99 (1H, m).

To determine the optical purity of 2-acetoxypropanal dimethyl acetal 11b it was transformed to (+)-MTPA ester by hydrolysis with NaOH followed by reaction with (+)-MTPA-Cl. The resulting (+)-MTPA ester was analyzed by $^1$H-NMR spectroscopy. The relative intensities of the methine group at 4.32 and 4.22 were used for ee determination. The same procedure was used for the resolution of 12a, except that vinyl valerate (1e of FIG. 2) and CCL were used. The methine group shifts of the MTPA ester at 4.38 and 4.17 ppm were used for ee determination.

EXAMPLE 7

PPL catalyzed transesterification of (±)-2-octanol (13a of Table 2) with vinyl acetate (1c in FORMULA 2)

520 mg (4 mmol) of 2-octanol (13a of Table 2) was dissolved in 8 mL of benzene along with 240 μL of dodecane as an internal standard. Two equivalents of vinyl acetate (1c in FORMULA 2) were added along with 520 mg of PPL. The suspension was stirred at 28° C. After the reaction had proceeded to 37%, the reaction suspension was worked as described in the general procedure. The products were separated on a silica gel column. The optical purities of isolated ester 2-octyl acetate (13b in Table 2) and 2-octanol (13a in Table 2) were determined by $^1$H-NMR spectroscopy in the presence of Eu(hfc)$_3$ (12 mg of acetate, or alcohol was added 84 mg or 72 mg of Eu(hfc)$_3$, respectively). The relative intensities of the methyl groups near the chiral center at 8.72 (major) and 8.64 (minor) (alcohol) and 4.3 (major) and 4.42 (minor) (ester) were used for ee determination. The ester was found to have an optical purity of 98% ee. In a similar manner, the esterification was allowed to proceed at 58% conversion and the unreacted alcohol was isolated. The alcohol was found to have an optical purity of >98% ee. The specific rotation of unreacted alcohol was +8.7° (c 1.0, CDCl$_3$) or +8.9° (neat). Authentic (S)-2-octanol from Aldrich: $[\alpha]^{17}$ +9° (neat). This result confirms that the unreacted alcohol has the "S" configuration. (R)-2-octyl acetate 13b: $^1$H-NMR (CDCl$_3$): 0.88 (3H, t, J=6.8 Hz); 1.20 (3H, d, J=6.2 Hz); 1.27 (8H, s); 1.41≅1.66 (2H, m), 2.02 (3H, s); 4.88 (1H, qt, J=6.2 Hz and 12.6 Hz).

EXAMPLE 8

PPL-catalyzed transesterification of sulcatol (14a in Table 2) with vinyl acetate (1c of FORMULA 2)

Compound (S)-14a (Table 2) is a useful pheromone, which has been prepared via lipase-catalyzed transesterification of the racemic alcohol using trichloroethyl propionate and trifluoroethyl laurate. Tambo, G. M. R., Schar, H-P., Busquets, X. F., Ghisalba, O. *Tetrahedron Lett.* 27 (1986) 5705–10; Belan, A., Bolte, J., Fauve, A., Gourey, J. G., Vaschambre, H. *J. Org. Chem.* 52, 256–60 (The latter is for synthesis of (S)-14a), Stokes, T. M., Oehlschlager, A. C. *Tetrahedron Lett.* 28 (1987) 2091–94 (trifluoroethyl laurate), and via alcohol dehydrogenase-catalyzed reduction of the ketone precursor. Tambo, G. M. R., Schar, H-P., Busquets, X. F., Ghisalba, O. *Tetrahedron Lett.* 27 (1986) 5705–10; Belan, A., Bolte, J., Fauve, A., Gourey, J. G., Vaschambre, H. *J. Org. Chem.* 52, 256–60 (The latter is for synthesis of (S)-14a). All of these processes give (S)-14a with >98% ee. The procedure described here using readily available vinyl acetate is faster and the product is easier to isolate.

513 mg (4 mmol) of sulcatol (14a in Table 2) was dissolved in 8 mL of benzene along with 240 μL of dodecane as an internal standard. Two eq (8 mmol) of vinyl acetate (1c of FORMULA 2) was added along with 512 mg of PPL. The suspension was stirred at 28° C. After the reaction had proceeded to 27%, the reaction was terminated and treated by the general procedures already described. The products were separated by silica gel column chromatography (CH$_2$Cl$_2$: n-hexane=0:1→1:4) giving acetate ester (14b of Table 2) and unreacted alcohol 14a. The optical purities of isolated sulcatol acetate and sulcatol were determined by $^1$H-NMR spectroscopy in the presence of Eu(hfc)$_3$. The relative intensities of methyl group near chiral center at 9.75 (major) and 9.56 (minor) (alcohol) and at 4.92 (major) and 5.02 (minor) (ester) were used for ee determination. The ester was found to have 98% ee.

In a similar manner, the esterification was allowed to proceed to 62% conversion and the unreacted sulcatol was isolated. The ee of unreacted sulcatol was found to be >98%. The specific rotation of unreacted alcohol was +15.1 (c 2, b, EtOH). [(S)-sulcatol; $[\alpha]^{25}_D$ +15.6° (c 0.015, EtOH)]. This result confirms that the unreacted alcohol had the spectrum "S" configuration. The $^1$H-NMR and the optical rotation of 14b corresponded to that reported for the "S" configuration of 14b. Tambo, G. M. R., Schar, H-P., Busquets, X. F., Ghisalba, O. *Tetrahedron Lett.* 27 (1986) 5705–10; Belan, A., Bolte, J., Fauve, A., Gourey, J. G., Vaschambre, H. *J. Org. Chem.* 52,256–60 (The latter is for synthesis of (S)-14a).

EXAMPLE 9

PPL-catalyzed transesterification of ferrocenylethanol (17a of Table 2) and vinyl propionate (1d of FORMULA 2) in toluene.

The resolution of ferrocenylethanol (17a of Table 2) represents an interesting example of enzyme-catalyzed kinetic resolution of chiral organometallic compounds. The ester (17b of Table 2) in aqueous ethanol decomposes via solvolysis to ferrocenylethyl ethyl ether and 17a. Gokel, G. W., Marquarding, D., Ugi, I. K. *J. Org. Chem.* 37 (1972) 3052–58. The acetate was subjected to SN$_1$ and SN$_2$ displacement. When the enzymatic resolution was carried out in aqueous solution, racemic 17a and 17b were obtained. The resolution therefore must be carried out in non-polar aprotic solvents such as toluene.

A mixture of ferrocenylethanol (17a of Table 2) (1 g, 4.4 mmol), vinyl propionate (1d of FORMULA 2) (6 mL, 52.8 mmol), and PPL (3 g) in toluene (25 mL) was shaken for 6 days. The reaction was stopped at ≅40% conversion (determined by NMR, based on the ratio of the methyl doublet of the reactant alcohol to that of the product ester). The mixture then was filtered to remove the enzyme and the liltrate was evaporated to give a mixture of products (0.72 g) which were separated by silica gel chromatography with hexane: ethyl acetate=5:1 v/v as the solvent system to give ferrocenylethyl propionate 17b ($[\alpha]_D$ −11.2 (c 1, EtOH)).

Ferrocenylethanol 17a (0.31 g, mp 70°–71° C., $[\alpha]_D^{25}$ +25.9 (c 1, benzene), lit[21] +30.1) prepared by a similar reaction proceeded to 60% conversion. The enantiomeric excesses of ferrocenylethanol 17a and ferrocenylethyl propionate 17b were determined to be 84% and 84%, respectively, with H-NMR in the presence of Eu(hfc)$_3$ (the methyl doublet of ferrocenylethanol 17a at 3.35 ppm and the methyl triplet of the acyl portion of the ester 17b at 2.82 ppm were measured). The configurations were determined to be "S"

for ferrocenylethanol 17a and "R" for ferrocenylethyl propionate 17b based on the rotation compared to the reported values. Gokel, G. W., Marquarding, D., Ugi, I. K. *J. Org. Chem.* 37 (1972) 3052–58. Ferrocenylethyl propionate 17b: $^1$H-NMR 1.10 (t, 3H), 1.55 (d, 3H), 2.30 (q, 2H), 4.2–4.44 (m, 9H), 5.80 (q, 1H). $^{13}$C-NMR (CDCl$_3$)9.22, 20.12, 27.92, 65.95, 67.92, 68.24, 68.70, 88.15, 173.89. The NMR data of ferrocenylethanol 17a were the same as reported. Gokel, G. W., Marquarding, D., Ugi, I. K. *J. Org. Chem.* 37 (1972) 3052–58. The acetate was subjected to SN$_1$ and SN$_2$ displacement. When the enzymatic resolution was carried out in aqueous solution, racemic 17a and 17b were obtained.

Structural Effect of Enol Esters

To compare the structural effect of different enol esters on the rate and stereoselectivity of the enzymatic transesterification, the resolution of solketal (10a of Table 2) using CCL as catalyst was performed. The results are shown in Table 3.

TABLE 3

Reaction rates and enantioselectivity of CCL-catalyzed transesterification of 10a with various acylating reagents[a] and of PPL-catalyzed reactions with 13[b].

| Ester | substrate | enzyme | Rel. Rate | % conversion | E[c] |
|---|---|---|---|---|---|
| CH$_3$CO$_2$Et | 10a | CCL | 1[d] | 16 | 1.2[e] |
| 1a | 10a | CCL | 20 | 42 | 1.4 |
| 1b | 10a | CCL | 8 | 44 | 2.7 |
| 1c | 10a | CCL | 62 | 37 | 1.4 |
| 1d | 10a | CCL | 122 | 53 | 2.0 |
| 1e | 10a | CCL | 13 | 23 | 3.1 |
| CH$_3$CO$_2$CH$_2$CF$_3$ | 10a | CCL | 1.5 | 34 | 1.4 |
| CH$_3$CO$_2$Et | 10a | CCL | 0.4 | — | — |
| 1a | 10a | CCL | 1700[g] | — | — |
| 1c | 13a | PPL | 5.5 | 58 | 96 |
| CH$_3$CO$_2$Et | 13a | PPL | 0.1 | 58 | 80 |
| H$_2$O | 13b | PPL | 60 | 58 | 90 |

[a]Reaction condition: the alcohol substrate (2 mmol) was dissolved in benzene (4 mL) along with 120 μL of dodecane as an internal standard. The acylating agent (2 eq) and CCL (265 mg) were added and the suspension was stirred at 28° C. At various intervals, the degree of conversion was determined by GC (20 m DB-5 megabore column; initial temperature, 80° C.; initial time, 1 minute; gradient, 10° C./min; flow rate 15 mL/min). After a certain degree of conversion, the reaction was terminated by filtration and the filtrate was evaporated. The residue was purified on a silica gel column (CH$_2$Cl$_2$: n-hexane = 1:3→1:0) to obtain the ester product. The optical purity of the product was determined by $^1$H-NMR in the presence of Eu(hfc)$_3$ (10 mg of acetate, propionate or pentanoate was added 40 mg, 40 mg or 28 mg of the shift agent, respectively).
[b]Conditions: for transesterification, PPL (520 mg), solvent (8 mL), substrate (4 mmol), acylating reagent (2 eq), temperature (28° C.). For hydrolysis, the same as above except that phosphate (0.1M, pH 7) was used as solvent.
[c]A measure of enantioselectivity determined by the method reported previously: Chen, C.-S.; Fujimoto, Y.; Girdaukas, G.; Sih, C. J. *J. Am. Chem. Soc.* 1982, 104, 7194.
[d]The initial rate was 0.8 μmol ester product formed per min per g of enzyme.
[e]The E value was obtained without considering the reverse reaction.
[f]The tributyl tin ether of glycerol acetonide was used as substrate.
[g]No transesterification was observed in 0.05M phosphate buffer at pH 7. The rate of hydrolysis of 1a was measured.

The reaction rate of enol ester was 10–100 times faster than ethyl acetate. Among the enol esters, vinyl esters reacted faster than isopropenyl esters and vinyl propionate was faster than vinyl acetate, but enol valerates were slower than enol acetates. The reaction rate of transesterification using different acylating reagents was compared to that of hydrolysis. As indicated in the resolution of 13 using PPL as catalyst, the relative rates for the hydrolysis of 13b and transesterification of 13a with vinyl acetate and ethyl acetate were found to be 600:55:1. The longer enol esters gave higher enantioselectivity. The lower selectivity in the ethyl acetate reaction may be due to the reversible nature of the reaction.

Effect of Organic Solvent

The effect of organic solvent on the CCL-catalyzed transesterification also was examined. As shown in Table 4, the rate of transesterification of glycerol acetonide (solketal) and isopropenyl acetate was slower in more polar solvents than in less polar solvents.

TABLE 4

Effect of organic solvent on CCL-catalyzed transesterifications of glycerol acetonide and 1a

| Reaction Solvent[a] | Relative Rate | E |
|---|---|---|
| Benzene | 50 | 1.4 |
| Isopropanyl acetate | 37 | 1.6 |
| Chloroform | 9 | 1.5 |
| Tetrahydrofuran | 1[b] | 1.5 |

[a]Reaction conditions are the same as those described in Table 2.
[b]The initial rate was 0.32 μmol ester formed per min per gram of enzyme.

All lipases tested were catalytically active in pyridine but inactive in DMF. In a study of the solvent effect on the activity of lipases in organic solvents, it was found that the rate of CCL-catalyzed acylation was enhanced in the presence of benzene.

Many valuable chiral synthons were prepared in high optical purity via lipase-catalyzed transesterification. The combination of two irreversible enzymatic processes, ester hydrolysis and ester synthesis, enabled effective syntheses of a number of optically active monoesters and alcohols in both enantiomeric forms, even with a moderately enantioselective enzyme. The same procedures also can be applied to the resolution of chiral ferrocenylethanol to prepare both enantiomers, a process which is impossible to accomplish in aqueous solution.

Lipases and cholesterol esterase were found to catalyze enantioselective ester syntheses in various organic media. The leaving groups (acetone and acetaldehyde) of enol esters used in the processes are volatile and easy to remove, making the product separation very simple. With regard to the rate of transesterification, vinyl esters were about 20–100 times faster than ethyl esters and about 5 times faster than isopropenyl esters, and generally the long chain esters were faster than short chain esters. As compared to lipase-catalyzed hydrolysis, vinyl esters reacted 10 times slower. Because the transesterification reaction is carried out in neutral apolar organic solvents, this procedure is suitable for acid-, base- or water sensitive substances.

Regioselective Acylations of Sugars and Their Derivatives

The methyl and higher glycosides of hexoses and pentoses are sufficiently soluble in pyridine or other less polar media such that the enzymatic acetylations of these compounds can be accomplished with lipase-catalysis. Stronger solvents such as N,N-dimethylformamide (DMF), dissolve many otherwise insoluble sugars but they also render the lipases inactive. Riva, S., Chapineau, J., Kieboom, A. P. G., Klibanov, A. M. *J. Am. Chem. Soc.* 110 (1988) 584–589. We have found that Protease N (neutral protease from Amano International Enzyme Company) will utilize enol esters as acyl donors. This enzyme also retains its catalytic activity in dry DMF.

Summaries of some of the data obtained with hexoses (Table 5), furanosides (Table 6), and nucleosides (Table 7) are shown hereinafter. Selected specific as well as general procedures for acetylation of sugars and their derivatives also are disclosed.

TABLE 5

Enzyme-catalyzed acetylation of hexoses and their derivatives using enol esters.

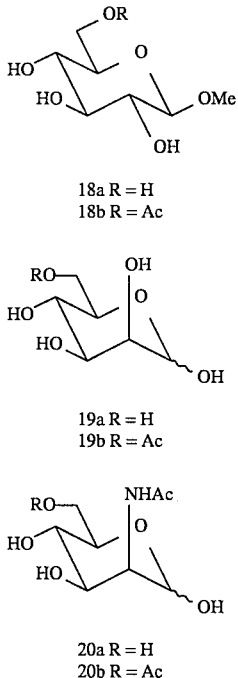

18a R = H
18b R = Ac

19a R = H
19b R = Ac

20a R = H
20b R = Ac

| Compound | ENZ | Enol ester | Conversion (%) | Regioselectivity (%) | Isolated Yield (%) |
|---|---|---|---|---|---|
| 18a | CCL | 1c | 30 | >98 | 23 |
| 19a | PN | 1a | 60 | >90 | 49 |
| 20a | PN | 1a | 85 | >90 | 73 |

TABLE 6

Lipase-catalyzed acetylation of furanosides.

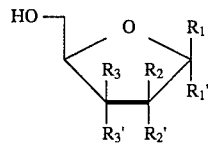

| | $R_1$ | $R_1'$ | $R_2$ | $R_2'$ | $R_3$ | $R_3'$ |
|---|---|---|---|---|---|---|
| 21 | (H, OMe) | | H | OH | H | OH |
| 22 | H | OMe | OH | H | H | OH |
| 23 | (H, OMe) | | H | OH | OH | H |
| 24 | (H, OMe) | | H | H | H | OH |

Parentheses indicate a mixture of anomers.

| | Product Yields[a] (%) | | | Regioselectivity |
|---|---|---|---|---|
| Substrate | 2-OAc | 3-OAc | 5-OAc | % |
| Methyl α,β-D-ribo-furanoside, 21 | 0 | 0 | 75–80[b] | 100 |
| Methyl α-D-arabino-furanoside, 22 | 0 | 0 | 75–80[b] | 100 |

TABLE 6-continued

Lipase-catalyzed acetylation of furanosides.

| Methyl α,β-D-xylo-furanoside, 23 | 0 | 0 | 60–85[b] | 100 |
| Methyl 2-deoxy-α,β-D-ribofuranoside, 24 | — | 17[c] | 39[d] | 78–100[e] |

[a]Yields reported are for anomeric mixtures.
[b]The anomeric products were separated to facilitate spectroscopic identification.
[c]The product obtained was methyl 3-O-acetyl-2-deoxy-β-D-ribofuranoside.
[d]The product consisted of a 9:1 mixture of α:β anomers.
[e]Regioselectivity was calculated based upon the individual anomers.

EXAMPLE 10

CCL-catalyzed transesterification of methyl β-D-glucopyranoside (18a of Table 5) with vinyl acetate (1c of FORMULA 2)

Methyl β-D-glucopyranoside (18a of Table 2) (388 mg, 2 mmol) and vinyl acetate (1c of FORMULA 2) (4 mmol) were dissolved in 12 mL of benzene—pyridine (2:1). Then 388 mg of CCL was added, and the suspension was stirred at 28° C. After 24 hours, an additional 388 mg of CCL was added, and this was repeated after 48 hours. The suspension was stirred at 28° C. for 5 days; then worked up as usual to afford methyl 6-O-β-D-glucopyranoside 18b as a solid, which was crystallized from ethyl acetate-n-hexane; m.p. 129°≅130° C.; $[\alpha]^{25}_D$ −27.1 (c 1.4, $CH_3OH$); $^1H$-NMR ($CD_3COCD_3$); 2.02 (3H, s); 2.98 (1H, s); 3.13≅3.25 (1H, m), 3.3≅3.55 (3H, m), 3.45 (3H, s), 4.15≅4.25 (2H, m); 4.30≅4.45 (3H, m); $^{13}C$-NMR ($CD_3COCD_3$); 104.56 (C1), 74.29 (C2), 77.36 (C3), 70.85 (C4), 74.33 (C5), 64.01 (C6), 20.42 and 170.69; (acetyl), 56.39 (methoxy).

Regioselective Acetylation of Methyl Pentofuranosides

The following general procedure was used for the substrates listed in Table 6.

To a solution of 1.64 g (10 mmol) of methyl pentofuranoside in a 24 mL of dry tetrahydrofuran containing a trace of hydroquinone was added 4.7 mL (50 mmol) of vinyl acetate (1c) and 5.0 g of porcine pancreatic lipase (PPL). The mixture was shaken in the dark at 37° C. on an orbital shaker at 250 rpm. The reaction was monitored by TLC. After 24–60 h the solution was filtered and the solids washed with fresh tetrahydrofuran. The filtrate and washings were evaporated in vacuo and the residue purified by silica gel chromatography using either chloroform-methanol or ethyl acetate-hexane mixtures as eluent. The regioselectivities and yield ranges for the specific reactions are listed in Table 6.

Protease-Catalyzed Reactions

Protease N obtained from Amano International Enzyme Co. was used on the following reactions. Other highly stable proteases, such as proteases obtained from thermophillic organisms or genetically engineered stable proteases, also could be used in the following reactions. The crude commercial preparation was dissolved in 0.1M phosphate buffer, pH 7.8 (2 g/35 mL) and lyophilized. The dry powder that was obtained was pulverized with a mortar and pestle prior to use.

Regioselective Acylation of Sugar

EXAMPLE 11

Preparation of 2-acetamido-6-O-acetyl-2-deoxy-D-mannopyranose

Protease N from BACILLUS SUBTILIS (obtained from Amano) (2 g) was dissolved in 0.1 mol $NaH_2PO_4$ (35 mL), and the resulting solution was stirred for 15 min. The pH was then adjusted to 7.8 with 8.0 NaOH and the solution was freeze-dried. This freeze-dried preparation was used in the synthetic procedure. N-acetyl-β-D-mannosamine monohydrate (Sigma) (478 mg, 2 mmol) was suspended in anhydrous N,N-dimethylformamide (2 mL). Isopropenyl acetate (600 mg, 6 mmol) was added followed by the enzyme preparation (600 mg). The suspension was shaken at 45° C. and monitored by TLC (silica gel; $EtOAc:MeOH:H_2O$= 100:10:1). After 44 h, the suspension was filtered and the enzyme washed with methanol (2×3 mL). The solvents were evaporated under vacuum at 40° C. to give a yellow syrup. This syrup was fractionated on a silica gel column (45 g) eluted with $EtOAc/MeOH/H_2O$ =100/10/1. Two products were obtained: the first with a higher $R_f$ corresponded to a triacetate compound (30 mg, 10%). The second (major) product was obtained as an amorphous white solid which, upon analysis was revealed to be 2-acetamido-6-O-acetyl-2-deoxy-D-mannopyranose. (384 mg, 73%): $^1$H-NMR ($D_2O$/p-dioxane=3.57 ppm) δ4.93 (s, H 1 α), 4.84 (s, H 1 β), 4.29-4.02 (m, 5 H), 3.87 (dd, H 3 α), 3.70-3.27 (m, 3 H), 1.95, 1.91, 1.88, and 1.87 (4 s, 6 H, acetal); $^{13}$C-NMR ($D_2O$/p-dioxane=67.46 ppm) δ176.60, 175.67, 174.96, and 174.92 (all carbonyls), 94.05 (c 1 β), 93.97 (C 1 α), 74.78 (c β), 72.72 (C β), 70.57 (C 5 α), 69.43 (C $^\alpha$), 67.94 (C α), 67.78 (C β), 64.61 (C 6 α), 64.36 (C 6 β), 54.84 (C 2 β), 54.18 (c 2 α); α/β=76/24; mp 47°–51° C.; $[\alpha]^{24}_D$ +15.9° (c 1.13 $H_2O$). Anal. Calcd for $C_{10}H_{16}NO_7$: C, 45.80; H, 6.15; N, 5.34. Found: C, 45.89; H, 6.20; N, 4.95.

Regioselective Acylation of Nucleosides

EXAMPLE 12

General Procedures

The following general procedures were used performing the regioselective acylation of nucleosides listed in Table 7:

1 mmol of nucleoside was dissolved in 2–4 mL of dry DMF and warmed. The solution was cooled to 45° C. and 1.1 mL (10 eq) of isopropenyl acetate and 260 mg of pulverized protease N were added. The suspension was shaken at 45° C. After the appropriate times, as indicated in Table 7, the reaction mixture was filtered and the liltrate was evaporated to dryness. The residue was purified by silica gel chromatography using mixtures of ethyl acetate:ethanol:water as the eluent for the times indicated. The isolated products were obtained in the yields shown in Table 7.

Table 7 indicates that, where acetylation occurred, the monoacetyl derivative was predominately formed. The preferential formation of the monoacetyl derivative indicates that the nucleoside was acetylated at the primary (5') hydroxyl group.

TABLE 7

Selective Enzymatic Acetylations of Nucleosides and Sugars in Anhydrous Dimethyl-Formamide

| Substrate | Enzyme | Time (days) | Mono-acetyl (%) | Di-acetyl (%) | Starting Material (%) |
|---|---|---|---|---|---|
| Guanosine | PN | 5 | 0 | 0 | 100 |
| Adenosine | PN | 1.75 | 40 | 0 | 60 |
| " | PN | 5 | 65 | <5 | 30 |
| 2-Deoxy adenosine | PN | 2 | 50 | — | — |
| 2-Deoxy adenosine | PN | 4 | 80 | — | — |
| Uridine | PN | 1.75 | 50 | 0 | 50 |
| " | PN | 5 | 80 | <5 | 15 |
| " | PN(pyr) | 5 | 60 | 0 | 40 |
| " | PN(THF) | 5 | 0 | 0 | 100 |
| " | PPL(pyr) | 3 | >95 | 0 | <5 |
| " | PPL(THF) | 3 | >95 | 0 | <5 |
| Cytidine | PN | 1.5 | 60 | 0 | 40 |
| " | PN | 3 | 80 | <5 | 15 |
| " | S | 3 | 0 | 0 | 100 |
| 2-Deoxycytidine | PN | 2 | 60 | — | — |
| " | PN | 4 | 80 | — | — |
| Thymidine | PN | 1.5 | 90 | 0 | 10 |
| " | S | 1.5 | 0 | 0 | 100 |
| Methyl 2-deoxy-D-ribofuranoside | PN | 2 | 70 | — | — |

PN = protease N [Amano]
S = subtilisin BPN
PPL = porcine pancreatic lipase

The simplicity of this irreversible transesterification makes the operation useful for the preparation of chiral alcohols or esters that may be difficult to prepare by other means.

The foregoing description has been for purposes of illustration. Those skilled in the art will appreciate a number of variations and modifications therefrom. The following claims are intended to cover all modifications and variations within the true spirit and scope of the present invention.

What is claimed is:

1. A method for preparing a regioselectively acylated alcohol, comprising:

mixing a chiral alcohol substrate selected from the group of nucleosides and sugars consisting of mannose, D-N-acetyl. mannosamine, adenosine, 2-deoxy-adenosine, uridine, cytidine, thymidine, methyl 2-deoxy-D-ribofuranoside, N-acetyl-D-mannosamine, and 2-deoxycytidine and an excess of enol ester selected from the group consisting of vinyl propionate, isoprenyl acetate, vinyl valerate, and vinyl acetate, in an organic solvent selected from the group consisting of anhydrous dimethylformamide and pyridine, to form a mixture;

incubating said mixture with a catalytic amount of protease; and isolating from said mixture an optically enriched regioselectively acylated form of said alcohol substrate.

2. The method of claim 1 wherein said protease is Protease N.

3. The method of claim 1 wherein said sugar is D-mannose.

4. The method of claim 1 wherein said enol ester is isopropenyl acetate.

5. The method of claim 3 wherein said solvent is anhydrous dimethylformamide.

6. The method of claim 1 wherein said sugar is D-N-acetyl-mannosamine.

7. The method of claim 6 wherein said enol ester is isopropenyl acetate.

8. The method of claim 6 wherein said solvent is anhydrous dimethylformamide.

9. The method of claim 1 wherein said solvent is anhydrous dimethylformamide.

10. The method of claim 9 wherein said nucleoside is guanosine.

11. The method of claim 9 wherein said nucleoside is adenosine.

12. The method of claim 9 wherein said nucleoside is 2-deoxy-adenosine.

13. The method of claim 9 wherein said nucleoside is uridine.

14. The method of claim 9 wherein said nucleoside is cytidine.

15. The method of claim 9 wherein said nucleoside is 2-deoxy-cytidine.

16. The method of claim 9 wherein said nucleoside is thymidine.

17. The method of claim 1 wherein said furanoside is methyl 2-deoxy-D-ribofuranoside.

18. The method of claim 10 wherein said sugar is N-acetyl-D-mannosamine monohydrate.

19. The method of claim 18 wherein said enol ester is isopropenyl acetate.

20. The method of claim 18 wherein said solvent is anhydrous dimethylformamide.

* * * * *